(12) United States Patent
Tanaka

(10) Patent No.: US 9,844,352 B2
(45) Date of Patent: Dec. 19, 2017

(54) RADIOGRAPHIC APPARATUS

(71) Applicant: SHIMADZU CORPORATION, Kyoto (JP)

(72) Inventor: Masahiro Tanaka, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 296 days.

(21) Appl. No.: 14/668,354

(22) Filed: Mar. 25, 2015

(65) Prior Publication Data

US 2016/0278720 A1    Sep. 29, 2016

(51) Int. Cl.
*A61B 6/04* (2006.01)
*A61B 6/00* (2006.01)

(52) U.S. Cl.
CPC .......... *A61B 6/0457* (2013.01); *A61B 6/0407* (2013.01); *A61B 6/4233* (2013.01)

(58) Field of Classification Search
CPC ... A61B 6/0457; A61B 6/4458; A61B 6/4464; A61B 6/548; A61B 6/0407; A61B 6/4233; A61B 6/027; A61B 6/032; A61B 6/0492; A61B 6/5205; A61B 6/5276; A61B 6/589; A61N 5/1049; A61N 5/103; A61N 5/1042; A61N 2005/1061; A61N 5/1031; A61N 2005/1087; A61N 5/1067; A61N 5/1037; A61N 5/10; A61N 5/1048; A61N 5/1038; A61N 2005/1054; A61N 5/1064; A61N 5/1065; A61N 5/107; A61N 5/1047; B66C 23/48; Y10T 74/20335; A61G 13/04; A61G 2203/36; A61G 2203/42; G06T 7/0012; Y10S 5/943

USPC ............ 378/20, 68, 62, 65, 208, 209, 196; 600/407; 250/453.11, 492.1
See application file for complete search history.

(56) References Cited

U.S. PATENT DOCUMENTS

2004/0172745 A1 * 9/2004 Hatfield ................. E03D 11/00
                                                        4/252.1
2005/0234327 A1 * 10/2005 Saracen ............... A61B 6/0457
                                                        600/407

FOREIGN PATENT DOCUMENTS

JP    2010012101    1/2010

* cited by examiner

*Primary Examiner* — Irakli Kiknadze
(74) *Attorney, Agent, or Firm* — Andrew F. Young, Esq.; Lackenbach Siegel, LLP

(57) ABSTRACT

A radiographic system provide a simple operation for table movement where the table revolves in one direction in accordance with an input of a revolving direction from a console driving the table upward vertically when one end of the table come close to a floor surface. The present invention also includes a system where the table moves downward vertically automatically, interlocking with a revolving of the table when the revolving direction is input to the revolving direction input means. According to the present invention, the table lifted along with revolving can be revolved or moved upward with an input operation in one system. Therefore, the operation of the radiographic apparatus can be easy.

14 Claims, 13 Drawing Sheets

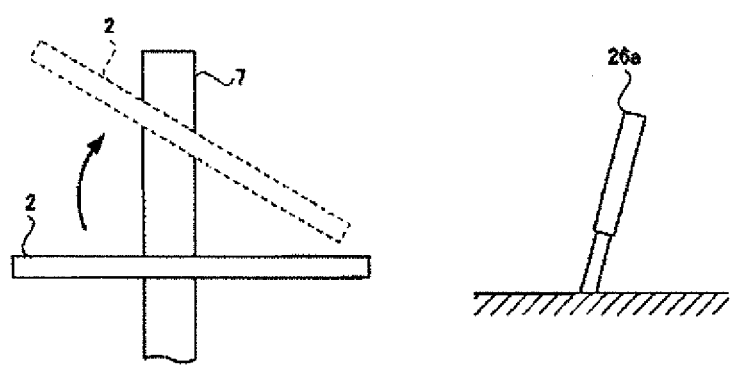
*Fig. 7A*    *Fig. 7B*

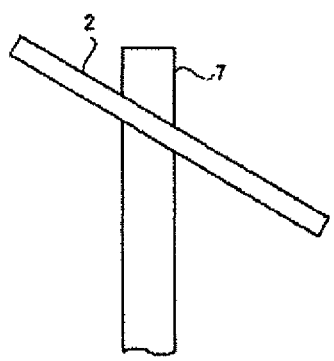 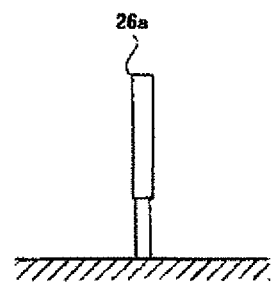
*Fig. 8A*  *Fig. 8B*

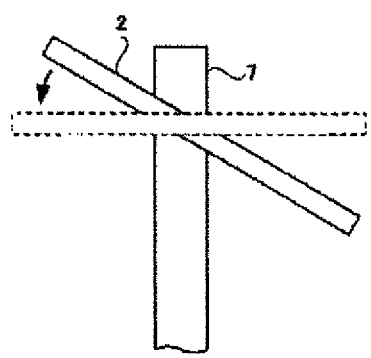 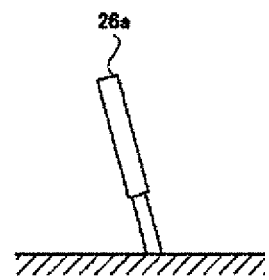
*Fig. 9A*  *Fig. 9B*

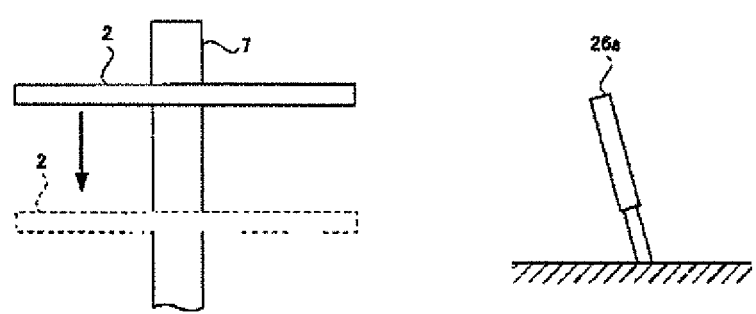
*Fig. 10A*        *Fig. 10B*

RADIOGRAPHIC APPARATUS

CROSS REFERENCE TO RELATED APPLICATIONS

This application relates to Japanese Ser. No. 2014-219439 filed Oct. 1, 2012, the entire contents of which are incorporated herein by reference.

FIGURE SELECTED FOR PUBLICATION

FIG. 1.

BACKGROUND OF THE INVENTION

Field of the Invention

The present invention relates to a radiographic apparatus and system conducting an imaging of a subject by irradiation and specifically relates to a radiographic apparatus, wherein a table on which the subject is laid can be tilted.

Description of the Related Art

A radiation apparatus to conduct imaging of a subject is equipped in a medical facility. Referring to FIG. 12, such radiation apparatus includes a radiation source 53 to irradiate radiation and a detector 54. A table 52 on which the subject M can be laid is equipped between the radiation source 53 and the detector 54 (e.g. referring to Patent Document 1.)

Such radiation apparatus comprises a system in which the table 52 can be tilted. The table 52 revolves around an axis C so that the subject on the table 52 can be tilted to the desired angle (specifically referring to FIG. 13.)

When the table 52 is just tilted, the end of the table 52 contacts the floor surface. Therefore, according to the conventional system, the table 52 moves upward in association with tilting of the table 52 while keeping the tilted state.

PRIOR ART DOCUMENT

Patent Document 1: JP Patent Published 2010012101 A1

ASPECTS AND SUMMARY OF THE INVENTION

Problems to be Solved by the Invention

According to one concern with conventional systems, the operator may not move the table easily so that the radiographic apparatus requiring complicated operation processes is only available.

For example, the operator may give a direction in order to tilt the table 52 in the horizontal position for the apparatus. According to the direction, the table 52 tilts and moves upward simultaneously and automatically. According to this operation, one end of the table 52 can be prevented from contacting the floor surface. Specifically, from the view of the operator, despite only giving the tilting direction for the table 52, the table 52 moves upward in association with tilt of the table 52.

Then, the operator gives the direction to the apparatus, by which the table 52 moved upward simultaneously in association with tilt will return to the original horizontal position. According to this direction, the table 52 tilts to the horizontal position.

According to a series of up-and-down operations, the table 52 moves upward from the original position. Specifically, when the operator tilts the table 52 from the horizontal position and then after returns to the horizontal position, the table 52 will never return to the original height. Such specification is originated in the idea in which it can be well accepted that the table 52 moves upward only when the table 52 tilts from the horizontal position to protect the apparatus from some damages. Specifically, when the table 52 returns to the horizontal position from tilted position, it is unnecessary that the table 52 moves up-and-down.

However, it is inconvenient unless the table 52 returns to the original position in the actual examination because there is an appropriate height for easy operation in accordance with the examination. Therefore, in the conventional system, the operator has to moves downward the table 52 moved up in association with up-and-down operation by the input operation through the different route from the tilt direction input. Specifically, the operator has to operate combinatorially (in a difficult combined manner) the input element of tilt direction and the element of up-and-down moving direction. Otherwise, the table 52 moved up-and-down from the horizontal position cannot be moved to the position before up-and-down operation. Specifically, the operation in the conventional system is remained complicated.

To solve the above problems, one purpose of the present invention is to provide an easily operative radiographic apparatus with a simple operation when a table 52 is moved up-and-down.

Means for Solving the Problem

The present invention comprises the following system to solve the above problem.

Specifically, a radiographic apparatus of the present invention comprises a radiation source irradiates radiation, a table on which a subject is laid and a detection means to detect the radiation transmitted through the subject, a revolving means to revolve the table around the revolving axis extending in the width direction of the table, a revolving direction input means to input the direction for revolving of the table, a revolving control means to control the revolving means according to the input by the revolving direction input means, a lifting means to move the table revolved by the revolving means in the vertical direction, and a lifting control means to control the lifting means to move the table upward vertically, when one end of the table comes closer to the floor surface of the examination room by revolving the table in one direction in accordance with an input of revolving direction input means, wherein the lifting control means is operative to move the table downward vertically when an input of the direction to revolve the table revolved in one direction in the opposite direction is input to the revolving direction input means.

A radiographic apparatus of the present invention comprises a system in which a table revolves in one direction in accordance with an input of revolving direction for the table and thereby the table moves upward vertically when one end of the table comes closer to the floor surface of the examination room. According to the present invention, in addition to this system, the radiographic apparatus further comprises a system in which the table moves downward vertically when the table revolved in one direction revolves in the opposite direction in accordance with an input to the revolving direction input means. Specifically, the radiographic apparatus comprises a system in which the table moves automatically downward vertically, interlocking with revolving of the table, when the revolving direction is input to the revolving direction means. According to the present invention, the table lifted along with revolving can be revolved and moved downward by an input operation in one system. Accordingly, the operator is not required to operate the radiographic apparatus with a combinatorial operation of a revolving direction input device of the table and an up-and-down moving direction input device so that the operation of the radiographic apparatus can be easier.

Further, according to the above radiographic apparatus, it is desirable that the revolving control means revolves the table until the end point angle at which revolving of the table ends and then the lifting control means moves the table downward vertically after revolving of the table reaches to the end point angle.

Action and Effects

The above system illustrates further specifically a radiographic apparatus of the present invention. Given the table is revolved until the end point angle at which revolving of the table ends and then the operation of the table is controlled to move downward vertically after revolving of the table reaches to the end point angle, the complex combinatorial operation in which revolving and moving downward of the table takes place simultaneously is not required so that the system of the present invention can be easily and surely brought in realization.

Further, according to the above radiographic apparatus, it is desirable that the revolving control means revolves the table until the horizontal level where the table is perpendicular to the vertical direction and then reverse revolving of the table can be ended.

The above system illustrates further specifically a radiographic apparatus of the present invention. According to the above system, given revolving of the table stops when the table is in the horizontal level, the head of the subject does not look downward so that the security therefor can be certainly assured.

Further, according to the above radiographic apparatus, it is further desirable that the revolving direction input means is operative as directed to revolve only while the operator continuously inputs the operation thereof and the revolving control means and the lifting control means suspends the operation of the table when the input operation to the revolving direction input means is suspended.

The above system illustrates further specifically a radiographic apparatus of the present invention. According to the above system, given the revolving direction input means is operative as directed to revolve only while the operator continuously inputs the operation thereof, revolving and moving downward of the table can be suspended only when the operator unlinks hands from the revolving direction input means so that a radiographic apparatus having an excellent operability can be provided.

Further, according to the above radiographic apparatus, it is further desirable that a selection input means is equipped, by which the selection whether the table should be moved downward vertically or not is input interlocking with the revolving control means.

The above system illustrates further specifically a radiographic apparatus of the present invention. Given the selection whether the table should be moved downward vertically or not is input, interlocking with the revolving control means, the movement mode of the table can be easily returned to established practice so that the radiographic apparatus having further flexible operability can be provided.

Further, according to the above radiographic apparatus, it is desirable that the lifting control means moves the table downward vertically to the end height at which the downward moving of the table ends.

The above system illustrates further specifically a radiographic apparatus of the present invention. According to the above lifting means, given the downward moving of the table ends when the table reached to the height where the downward moving of the table ends, the table can be easily returned to the predetermined height. Accordingly, the table can be easily returned to the initial state before the table moves up-and-down so that a radiographic apparatus having easy operability can be provided.

Effects of the Invention

A radiographic apparatus of the present invention comprises a system in which a table revolves in one direction in accordance with an input of revolving direction for the table and thereby the table moves upward vertically when one end of the table comes closer to the floor surface of the examination room. In addition to the above system, the present invention further comprises a system in which the table moves automatically downward vertically, interlocking with revolving of the table, when the revolving direction is input to the revolving direction means. According to the present invention, the table lifted along with revolving can be revolved and moved downward by an input operation in one system. Therefore, the operation of the radiographic apparatus can be easily operated.

BRIEF DESCRIPTION OF THE DRAWINGS

FIGS. 7A and 7B are a schematic diagram illustrating an operation of the X-ray radiographic apparatus of Embodiment 1.

FIGS. 8A and 8B are a schematic diagram illustrating an operation of the X-ray radiographic apparatus of Embodiment 1.

FIGS. 9A and 9B are a schematic diagram illustrating an operation of the X-ray radiographic apparatus of Embodiment 1.

FIGS. 10A and 10B are a schematic diagram illustrating an operation of the X-ray radiographic apparatus of Embodiment 1.

DETAILED DESCRIPTION OF THE PREFERRED EMBODIMENTS

Figure 1:
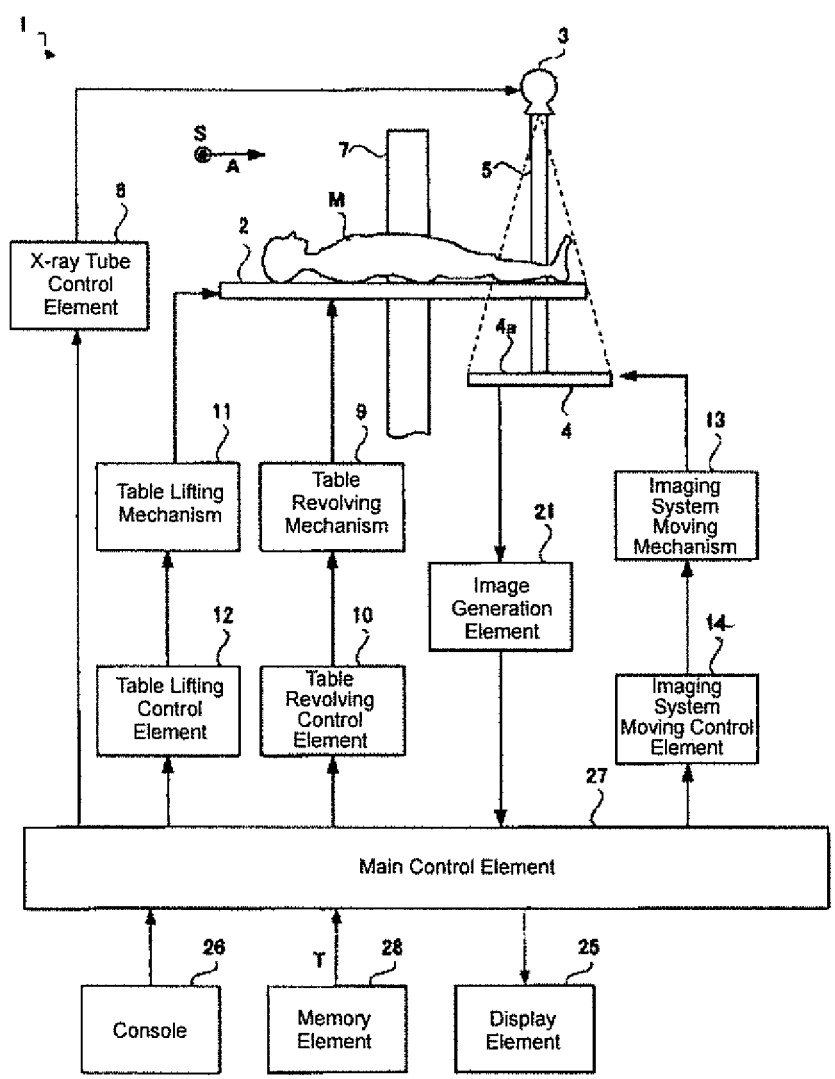
FIG. 1 is a functional block diagram illustrating the total system of the X-ray radiographic apparatus of Embodiment 1.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) teens may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

An X-ray of Embodiment is the radiation of the present invention but the invention is not limited to this X-ray form only and may include other wavelengths of emission. In addition, FPD stands for Flat Panel Detector. The X-ray radiographic apparatus of the present invention is particularly for a urinary examination but may be otherwise used for examination of other forms.

Total System of the X-Ray Radiographic Apparatus

First, the inventor illustrates the system of the X-ray radiographic apparatus of Embodiment 1. Referring to FIG. 1, an X-ray radiographic apparatus comprises a table 2 on which a subject M in the supine position is laid, an X-ray tube 3 to irradiate an X-ray is mounted above the table 2 and the FPD 4 to detect the X-ray transmitted through the subject M is mounted under the table 2. The FPD 4 has a rectangular shape with 4 sides along with either the axis direction A of body or the side direction S of body of the subject M. Further, the X-ray tube 3 irradiates the X-ray quadrangular pyramid beam radiating out therefrom to the FPD 4. The FPD 4 receives the X-ray beam on the whole surface thereof. X-ray detection elements are arrayed two-dimensionally in the axis direction A of body and the side direction S of body on the detection surface 4a of the FPD 4, which detects the X-ray. The X-ray tube 3 corresponds to the radiation source of the present invention and the FPD 4 corresponds to the detection means of the present invention.

Figure 2:
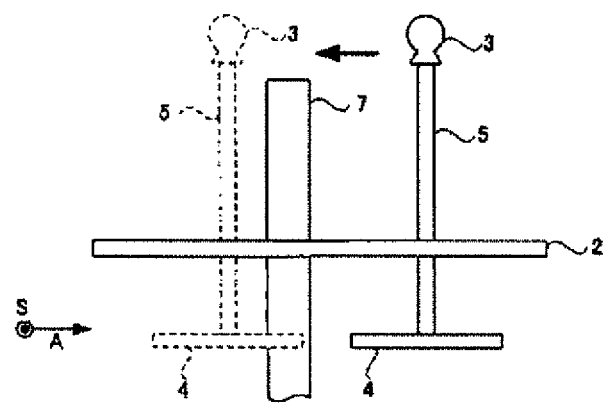
FIG. 2 is a schematic diagram illustrating an operation of the X-ray radiographic apparatus of Embodiment 1.

A stand 5 supports an imaging system 3, 4 comprising the X-ray tube 3 and the FPD 4. The stand 5 can be driven by the imaging system moving mechanism and moved in the axis direction A of body of the subject M against the table 2. Accordingly, the imaging system moving mechanism is the mechanism by which the X-ray tube and the FPD 4 move against the table 2 in an integrated manner in the longitudinal direction of the table 2. According to such moving, the X-ray imaging position for the subject M can be changed. The imaging system moving control element 14 is installed to control the imaging system moving mechanism 13. FIG. 2 is illustrating the manner in which the imaging system moving mechanism 13 moves the imaging system 3, 4 together with the stand 5. Accordingly, even when the imaging system moving mechanism 13 moves, the positional relationship between the X-ray tube 3, the FPD 4 and the stand 5 will not change.

A table support member 7 is the member vertically extending from the floor surface of the examination room and supports the table 2 with freedom of revolving and freedom of lifting. First, the inventor illustrates the manner in which the support 7 supports the table 2 with freedom of revolving. Revolving of the table 2 can be conducted by a table revolving mechanism 9 installed to the table support 7. The table revolving control element 10 is installed to control the table revolving mechanism 9. The table revolving control element 10 comprises a system to control the table revolving mechanism 9 in accordance with input to the console 26. The table revolving mechanism 9 corresponds to the revolving means of the present invention and the table revolving control element 10 corresponds to the revolving control means of the present invention.

Figure 3:
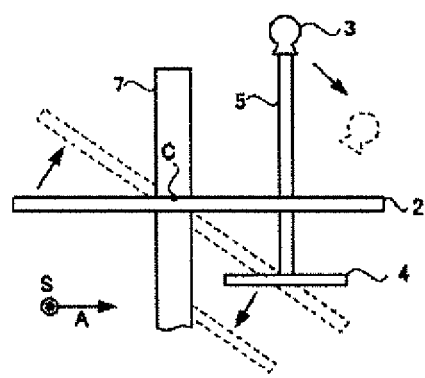
FIG. 3 is a schematic diagram illustrating an operation of the X-ray radiographic apparatus of Embodiment 1.

FIG. 3 is illustrating the manner in which the table 2 revolves in one direction around the axis C by the table revolving mechanism 9. The axis C is extending in the width direction (side direction S of body of the subject M) of the table 2. The table revolving mechanism 9 can also reversely revolve the table 2 revolved in one direction. A purpose of illustration of FIG. 3 is to illustrate the system of the table revolving mechanism 9. As illustrated later, it should be noted that the actual moving aspect of the table 2, when the table 2 revolves, is different from the manner indicated in FIG. 3.

The notable point in FIG. 3 is that the imaging system 3, 4 also revolves along with revolving when the table 2 revolves. Specifically, the table revolving mechanism 9 supports not only the table 2 but also the stand 5 and the imaging moving mechanism 13 in an integrated manner and the stand 5 revolves while keeping the relative positional relationship with the table 2 when the table 2 revolves. Accordingly, the imaging system 3, 4 revolves along with the table 2 while keeping the relative positional relationship with the table 2. Accordingly, the table revolving mechanism 9 revolves the table 2, the X-ray tube 3 and the FPD 4 around the axis C extending in the width direction of the table 2 while keeping the positional relationship each other. Further, the positional relationship between the axis C and the table 2 does not change along with driving of the imaging system moving mechanism 13. Specifically, the positional relationship between the table revolving mechanism 9 and the table 2 does not change according to the imaging system moving mechanism 13.

Next, the inventor illustrates the manner in which the support member 7 supports the table 2 with freedom of lifting. Lifting of the table 2 can be conducted by a table lifting mechanism 11 installed to the table support member 7. The table lifting control element 12 is installed to control the table lifting mechanism 11. The table lifting mechanism 11 corresponds to the lifting means of the present invention and the table lifting control element 12 corresponds to the lifting control means of the present invention.

Figure 4:
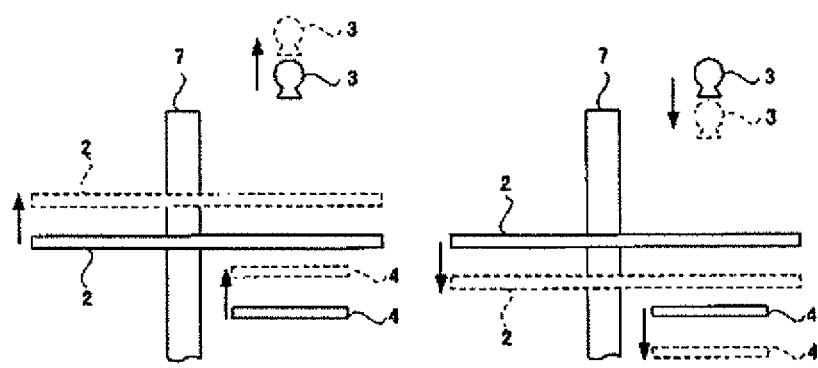
FIGS. 4A and 4B are a schematic diagram illustrating an operation of the X-ray radiographic apparatus of Embodiment 1.

FIGS. 4A and 4B illustrate the manner in which the table lifting mechanism 11 moves the table 2 up-and-down. The left side (FIG. 4A) illustrates the manner in which the table lifting mechanism 11 attached to the table support 7 extends in the vertical direction and thereby the table 2 moves upward vertically. The right side (FIG. 4B) illustrates the manner in which the table lifting mechanism 11 attached to the table support 7 shortens in the vertical direction and thereby the table 2 moves downward in the vertical direction.

The notable point in FIGS. 4A and 4B is that the imaging system 3, 4 also lifts along with lifting when the table 2 lifts. Specifically, the table lifting mechanism 11 supports not only the table 2 but also the stand 5, the imaging moving mechanism 13 and the table revolving mechanism 9 in an integrated manner and the stand 5 lifts while keeping the relative positional relationship with the table 2 when the table 2 lifts. Accordingly, the imaging system 3, 4 lifts along with the table 2 while keeping the relative positional relationship with the table 2. Accordingly, the table lifting mechanism 11 lifts the table 2, the X-ray tube 3 and the FPD 4 which are revolved by the table revolving mechanism 9 in the vertical direction while keeping the positional relationship each other.

The positional relationship between the table 2 and the imaging system 3, 4 will be kept without changing even when the table 2 moves in the mixed moving of revolving and lifting. The positional relationship between the table 2 and the imaging system 3, 4 changes depending on the imaging system moving mechanism 13 but does not change depending on the table revolving mechanism 9 and the table lifting mechanism 11.

Figure 5:
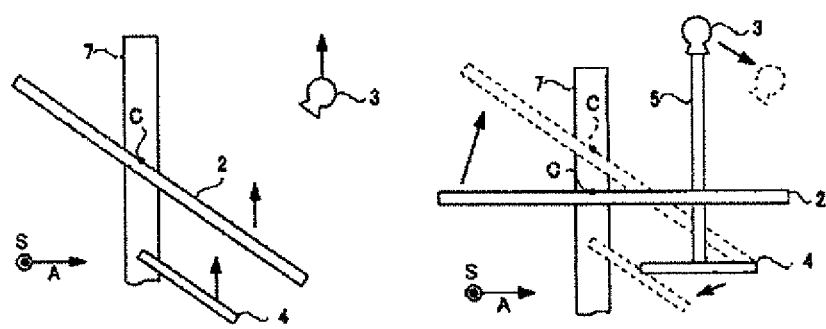
FIGS. 5A and 5B are a schematic diagram illustrating an operation of the X-ray radiographic apparatus of Embodiment 1.

Collaborative Operation of the Table Revolving Control Element and the Table Lifting Control Element A table lifting control element 12 of the present invention is operative collaboratively with the table revolving control element 10. The left side (FIG. 5A) illustrates the manner in which the table 2 is tilted by the table revolving control element 10. At this time, one end of the table 2 moves downward in the vertical direction, and comes closer to the floor of the examination room. Given revolving of the table 2 continues, the likelihood of that one end of the table 2 contacts the floor surface would emerge. Given this factor, according to the system of the present invention, the table lifting control element 12 moves the tilted table 2, as illustrated by the arrow in the left side (of FIG. 5A), moves upward in the vertical direction. Accordingly, the table 2 will never contact the floor surface. In addition, the X-ray tube 3 and the FPD 4 move upward in the vertical direction following moving of the table 2. Specifically, according to the system of the present invention, the table lifting control element 12 controls the lifting mechanism 11 to move the table 2 upward vertically when one end of the table 2 comes closer to the floor surface of the examination room following revolving of the table 2, which takes place in one direction in accordance with an input to a console 26.

Such operation becomes really operative when the table revolving control element 10 outputs the revolving angle of the table 2 to the table lifting control element 12. The table revolving control element 10 sequentially outputs the revolving angle thereof to the table lifting control element 12 when the table 2 revolves. The table lifting control element 12 retrieves the relational table stored in the memory element 28 between the revolving angle and the height of the table 2 and determines the height corresponding to the current revolving angle of the table 2 from the table. The table lifting control element 12 compares the actual height of the table 2 with the determined height thereof and then moves the table 2 upward to the determined actual height is lower than the determined height. Such moving operation for the table 2 is conducted in real time in accordance with revolving of the table 2.

Specifically, according to the radiographic apparatus of the present invention, when the table 2 revolves, the table 2 moves automatically upward following revolving. In fact, it is obvious that the table 2 shown by the solid line in the right side (FIG. 5B) revolves and moves upward in the vertical direction to the broken line position following the collaborative operation of the table revolving control element 10 and the table lifting control element 12. Further, referring to FIGS. 5A, 5B, it is obvious that the axis C, the X-ray tube and the FPD 4 move following moving of the table 2. Thus, the collaborative operation of each element 10, 12 is conducted when the table 2 revolves in one direction and then one end of the table 2 comes closer to the floor surface of the examination room.

Figure 6:
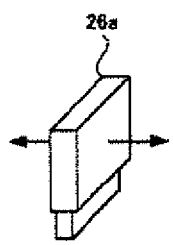
FIG. 6 is a schematic diagram illustrating a structure of the console of Embodiment 1.

A radiographic apparatus according to Embodiment 1 comprises a console 26 to which the operator's direction is input. Further, the console 26 comprises a table revolving switch 26a in association with the table revolving control. The table revolving switch 26a is operative to input the operator's direction as to a tilt direction and a tilt level of the table 2. Referring to FIG. 6, the table revolving switch 26a is operative to input the operator's direction by flipping the frame from side to side. For example, when the operator flips the frame to left, the table 2 revolves in a counterclockwise direction by the table revolving mechanism 9 and then tilts. When the operator unlinks a hand, the frame returns to the prior position to tilt thereof and then the tilting of the table 2 is held. Also, when the operator flips the frame to the right, the table 2 revolves in a clockwise direction by the table revolving mechanism 9 and then tilts. When the operator unlinks a hand, the frame returns to the prior position to tilt thereof and then the tilting of the table 2 is held. The revolving direction input means of the present invention can be actually conducted with the table revolving switch 26a. Thus, it is the system in which the direction to revolve the table 2 is input through the table revolving switch 26a. The table revolving switch 26a is corresponding to the revolving direction input means.

Table Revolving Operation Using the Table Revolving Switch

Next, the inventor illustrates the manner in which the table 2 actually revolves by the operation of the table revolving switch 26a. FIGS. 7A, 7B illustrate the moving aspect of the table 2 in association with the table revolving switch 26a. Referring to FIG. 7A, when the table 2 is in parallel position to the floor surface of the examination room and in the horizontal level, the operator tilts the table revolving switch 26a to one direction (to the right), the input of the table revolving switch 26a is transmitted to the table revolving control element 10 and by following the input, the table revolving control element 10 revolves the table 2 in one direction (clockwise direction.) Then, the table revolving control element 10 transmits the revolving angle to the table lifting control element 12 in real time and by following the input, the table lifting control element 12 becomes operative. Thus, the table 2 moves in combination of revolving and lifting and moves from the solid line position to the broken line position as shown in the left side of FIG. 7A by the collaborative operation of the table revolving control element 10 and the table lifting control element 12.

When the operator unlinks a hand from the table revolving switch 26a, the frame the table revolving switch 26a returns to the prior position to tilt thereof and then revolving of the table 2 is held. FIGS. 8A, 8B show the holding position of revolving and lifting of the table 2 with the switch.

FIGS. 9A, 9B illustrates the manner in which the table 2 in the tilted position in FIG. 8 revolves toward the opposite direction of the previous position. Referring to FIG. 9A, the operator tilts the table revolving switch 26a to the opposite direction (to left), the input of the table revolving switch 26a is transmitted to the table revolving control element 10 and by following the input, the table revolving control element 10 revolves the table 2 in the opposite direction (counter-clockwise direction.) And then, the table 2 returns to the horizontal level, shown as the broken line in FIG. 9A. Once the table 2 returned to the horizontal level, even if the operator further tilts the table revolving switch 26a, the table 2 will not revolve further. Specifically, the table revolving control element 10 comprises the system in which the table 2 revolves until the end angle that is the angle at which revolving of the table 2 ends. Further, according to Embodiment 1, the table revolving control element 10 revolves the table 2 until the horizontal level where the table 2 is perpendicular to the vertical direction and then reverse revolving of the table can be ended.

At this time, even though the table 2 returns to the horizontal level by revolving, the height of the table is remained higher than the initial height, comparing the height in FIG. 7A. The present invention is characterized in the best mode in which moving of the table 2 is illustrated afterward. Specifically, even if the operator tries to continuously tilt the table revolving switch 26a to the opposite direction (to left) despite the horizontal position thereof, the table revolving control element 10 does not further revolve the table 2 but instead transmits the input information of the table revolving switch 26a to the table lifting control element 12. And then, the table lifting control element 12 moves the table 2 downward vertically until the initial height in FIG. 7A.

Specifically, the table lifting control element 12 moves the table 2 downward vertically after revolving of the table 2 reaches to the end angle. And then, when the table 2 returns to the initial position, the table will never move or revolve even if the table revolving switch 26a is being continuously tilted to the opposite direction (to the left).) Accordingly, the table lifting control element 12 moves the table 2 downward vertically to the end height at which the downward moving of the table 2 ends. According to Embodiment 1, the table lifting control element 12 moves the table 2 downward to the initial position where the table 2 is prior to up-and-down operation.

Thus, the table lifting control element 12 is characterized in that the table 2 moves downward vertically when an input by which the table 2 revolved in one direction and moved upward is revolved in the reverse direction is provided to the console 26 through the table revolving switch 26a. Specifically, the table revolving switch 26a of the present invention comprises the system in which a direction as to not only revolving of the table but also temporarily moving downward of the table can be input.

Further, the console 26 is operative in the manner in which the direction of revolving is input only while the input operation by the operator is continuously provided through the table revolving switch 26a, and when the input to the console 26 is suspended, the table revolving control element 10 and the table lifting control element 12 suspend the operation of the table 2.

Default Value Required for Table Revolving Operation

Consequently, the inventor sets forth the default value required for the above operation. Firstly, the table revolving control element 10 must be operative referring to the default value of the end angle at which revolving of the table 2 is banned. According to the above specific Embodiment, the default value of the end angle is the default value at which reverse revolving of the table 2 beyond null is banned. Referring to the default value, the table revolving control element is operative so that the table 2 in the horizontal position cannot revolve in the opposite direction. The default value of the end angle is stored in the memory element 28 and can be changed by an input to the console 26, accordingly. The table revolving control element 10 can be operative by retrieving the default value of the end angle stored in the memory 28.

Next, the table lifting control element 12 must be operative referring to the default value of the end height (the initial height) at which lifting of the table 2 ends. According to the above specific Embodiment, the default value of the end height is the default value providing the height of the table 2 before revolving the table, and specifically, it is the height in the default position from the floor surface of the examination room to the table 2 as shown in the solid line in FIG. 7A. The table lifting control element 12 is operative referring to the default value so that the table 2 can be in the vertical position following revolving, as illustrated in FIGS. 10A, 10B, and downward moving of the table 2 can be limited when the table 2 is operative to move downward. Specifically, the table 2 can never move downward beyond the height provided by the default value of the end height. The default value is stored in the memory element 28 and can be changed by an input from the console 26, accordingly. The table lifting control element 12 can be operative by retrieving the default value of the end height stored in the memory 28.

Other Elements

Next, the inventor sets forth other elements in the system of the X-ray radiographic apparatus. The purpose of an X-ray tube control element 6 is to control parameters including a tube current electricity of the X-ray tube, a tube electric pressure and an irradiation and exposure time. The FPD 4 detects an X-ray that is radiated from the X-ray tube and transmitted through the subject M and then generates the detection signal. The generated signals are output to the image generation element 21 and the image incorporating the projection images of the subject M are generated therefrom.

The purpose of the display element 25 is to display each image acquired by X-ray radiography. The purpose of the console 26 is to input the direction for starting the radiation and so forth by the operator and the direction for moving the imaging system 3, 4 as for the table 2, in addition to the above operation input. Further, the main control element 27 is installed to comprehensively control each control element. The main control element comprises a CPU and executes a variety of programs to run each control element 6, 10, 12 and image generation element 21. Further, each above element can be separately run in each operational element executing such program. The memory element 28 stores parameters related to the table, revolving and lifting of the table 2.

A radiographic apparatus of the present invention comprises the system in which a table 2 revolves in one direction in accordance with an input of revolving direction for the table 2 to a console 26 and thereby the table 2 moves upward vertically when one end of the table 2 comes closer to the floor surface of the examination room. According to the present invention, in addition to this system, the radiographic apparatus further comprises the system in which the table 2 moves downward vertically when the table 2 revolved in one direction revolves in the opposite direction in accordance with an input to the console 26. Specifically, the present invention further comprises the system in which the table 2 moves automatically downward vertically, interlocking with the revolving of the table 2, when the revolving direction is input from the revolving direction means. According to the present invention, the table 2 lifted along with revolving can be revolved or moved downward by an input operation in one system. Accordingly, the operator is not required to operate the radiographic apparatus with a combinatorial operation of the revolving direction input device of the table and the up-and-down moving direction input device so that the operation of the radiographic apparatus can be easier.

Given the table is revolved until the end point angle at which revolving of the table ends and then the operation of the table is controlled to move downward vertically after revolving of the table reaches to the end point angle, the complex combinatorial operation, in which revolving and moving downward of the table must take place simultaneously, is not required so that the system of the present invention can be easily and surely brought in realization.

According to the above system, given revolving of the table 2 stops when the table 2 is in the horizontal level, the head of the subject M does not look downward so that the security thereof can be certainly assured.

According to the above system, given the console 26 is operative as directed to revolve only while the operator is continuously running input operation thereof, revolving and moving downward of the table 2 can be suspended only in the event of that the operator unlinks hands from the revolving direction input means so that a radiographic apparatus having an excellent operability can be provided.

According to the above table lifting control element 12, given the downward moving of the table 2 ends when the table 2 reaches to the height where the downward moving of the table ends, the table 2 can be easily returned to the predetermined height. Accordingly, the table 2 can be easily returned to the initial state before the table 2 moves up-and-down so that a radiographic apparatus having easy operability can be provided.

The present invention is not limited to the above system and further another alternative Embodiment can be implemented.

Figure 11:
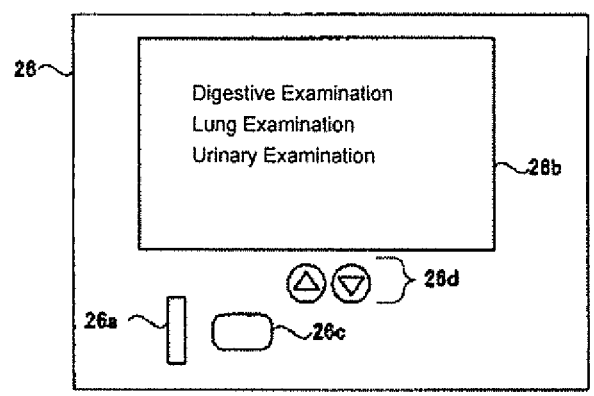
FIG. 11 is a plan view illustrating the system of X-ray radiographic apparatus of an alternative Embodiment of the present invention.
Figure 12:
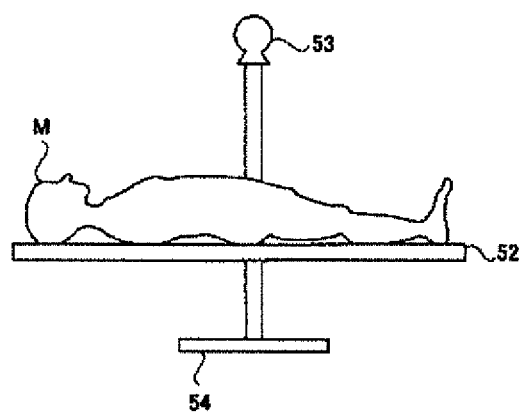
FIG. 12 is a schematic diagram illustrating an operation of the conventional X-ray radiographic apparatus.
Figure 13:
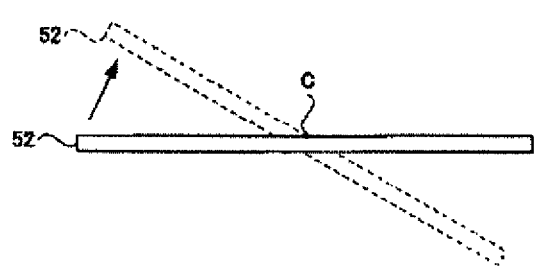
FIG. 13 is a schematic diagram illustrating an operation of the conventional X-ray radiographic apparatus.

(1) In addition to the above system, referring to FIG. 11, the console 26a may equip with an operation panel 26b. The radiographic mode to show the purpose is displayed on the operation panel 26b when the radiography is conducted. The operator can transmit the next scheduled examination to the apparatus by selecting one from radiographic modes. Accordingly, the operator can set up suitable parameters for the radiography just by selecting the radiographic mode even without manual input of a variety of parameters as to the radiography one by one. The radiographic mode displayed on the operation panel 26b is, for example, for a urinary system examination and so forth. Thus, the console 26 is the system in which the operator enters the radiographic mode. The default value of end angle and the default value of end height, referred by the table revolving control element 10 and the table lifting control element 12, may be added to parameters in association with the radiographic mode.

(2) In addition to the above system, referring to FIG. 11, the console 26 may equip with a changing-over switch 26c. The changing-over switch 26c is used to input the operator's direction as to whether the table lifting control element 12 should be interlocked with the table revolving control element 10 or not. When the changing-over switch 26c is turned on, the table 2 moves downward automatically by the table lifting control element 12. On the other hand, the changing-over switch 26c is turned off, the table lifting control element 12 never moves the table 2 downward regardless the operation of the table revolving control element 10. Specifically, when the changing-over switch 26c is off, revolving of the table 2 can be conventionally operative. Thus, the selection as to whether the table 2 should be moved downward vertically, interlocking with the table revolving control element 10, through the changing-over switch 26e is input to the console 26.

According to the alternative Embodiment, given the selection whether the table 2 should be moved downward vertically or not is conducted, interlocking with the revolving control element 10, the moving mode of the table 2 can be easily returned to established practice so that an radiographic apparatus having further flexible operability can be provided.

(3) In addition to the above system, referring to FIG. 11, the console 26 may equip with the up-and-down button 26d in order to set up the initial height of the table 2. Accordingly, the operator can easily change the default value of the initial height referred by the table lifting control element 12.

Having described several features and details of the proposed apparatus, system, and method of operation it will be readily apparent that the invention is not so limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

It is additionally intended that the proposed apparatus and system and noted step-flow-chart for methods of operation and use and adjustment will be recognized herein. For further example, the proposed mechanisms, memory elements, display elements, moving elements, gearing, hydraulics, drive members, consoles, etc. will be understood to include all operational features required to achieve the noted functions, steps, features, and goals herein, such that the computer processors and processing controllers, and all related communication linkages, ports, memory programs, protocols, communication pathways, input and output features will be understood by those of skill in the art sufficient to operatively enable the proposed functional features and modes, means, and steps herein.

EXPLANATION OF REFERENCES

2 Table
3 X-ray tube (radiation source)
4 FPD (detection means)
9 Table revolving mechanism (revolving means)
10 Table revolving control element (revolving control means)
11 Table lifting mechanism (lifting means)
12 Table lifting control element (lifting control means)
26 Console (revolving direction input means, selection input means)

What is claimed is:
1. A radiographic apparatus, comprising;
a radiation source irradiates a radiation;
a table on which a radiographic subject is laid;
a detection means operative to detect the radiation transmitted through the subject;
a revolving means to revolve said table around a revolving axis extending in a width direction of said table;
a revolving direction input means operative to input a direction for revolving of said table;
a revolving control means to operatively control said revolving means according to the input of said revolving direction input means;
a lifting means to move said table revolved by said revolving means in the vertical direction;

a lifting control means to control said lifting means to move said table upward vertically when one end of said table comes closer to a floor surface of the examination room following a revolving of said table in one direction in accordance with an input of said revolving direction input means, an input information send control means that sends an input information that is provided to said revolving direction input means and to said lifting control means when an input by which said table revolved in a first direction is revolved in a reverse direction is provided to said revolving direction input means and a revolving angle of the table coinciding with a predetermined end angle is detected; and wherein said lifting control means is operative to move said table downward vertically based on said input information sent from said input information send control means.

2. A radiographic apparatus according to claim 1, wherein:

said table revolving control element revolves said table until an end angle that is an angle at which revolving of said table ends, and said lifting control means moves said table downward vertically after revolving of said table reaches to the end angle.

3. A radiographic examination apparatus, according to claim 2, wherein:

said revolving control means operatively revolves said table until the horizontal level where the table is perpendicular to the vertical direction and then reverse revolving of said table is ended.

4. A radiographic apparatus according to claim 3, wherein:

said revolving direction input means is operative only in the event of that an external operator is operative to continuously conducting an input operation as the direction of revolving is provided; and said revolving control means and said lifting control means are operative to suspend the operation of said table when the input operation is suspended at said revolving direction means.

5. A radiographic apparatus according to claim 4, further comprising;

a selection input means, and wherein a selection is operative to determine whether said table should be moved downward vertically or not interlocking with said revolving control means.

6. A radiographic apparatus according to claim 5, wherein:

said lifting control means is operative to move said table downward vertically to the end height at which a downward moving of said table ends.

7. A radiographic system, comprising;

a radiation source irradiates a radiation;

a table on which a radiographic subject is laid;

a detection means operative to detect the radiation transmitted through the subject, the radiation source and the detection means being in a fixed relative position with respect to each other;

a stand supporting and coupling the radiation source and the detection means to one another;

a revolving means to revolve said table around a revolving axis extending in a width direction of said table;

a revolving direction input means operative to input a direction for revolving of said table;

a revolving control means to operatively control said revolving means according to the input of said revolving direction input means;

a lifting means to move said table revolved by said revolving means in the vertical direction, the lifting means supporting the table and the stand such that when the lifting means effects movement of the table, the stand, the radiation source, and the detection source correspondingly move;

a lifting control means to control said lifting means to move said table upward vertically when one end of said table comes closer to a floor surface of the examination room following a revolving of said table in one direction in accordance with an input of said revolving direction input means, the lifting means supporting the table and the stand such that when the lifting control means effects movement of the table, the stand, the radiation source, and the detection source correspondingly move;

an input information send control means that sends an input information that is provided to said revolving direction input means and to said lifting control means when an input by which said table revolved in a first direction is revolved in a reverse direction is provided to said revolving direction input means and a revolving angle of the table coinciding with a predetermined end angle is detected;

wherein said lifting control means is operative to move said table downward vertically based on said input information sent from said input information control means;

said table revolving control element revolves said table until an end angle that is an angle at which revolving of said table ends, and said lifting control means moves said table downward vertically after revolving of said table reaches to the end angle;

said revolving direction input means is operative only in the event of that an external operator is operative and to continuously conducts an input operation as the direction of revolving is provided; and said revolving control means and said lifting control means are operative to suspend the operation of said table when the input operation is suspended at said revolving direction means.

8. A radiographic system according to claim 7, further comprising;

a selection input means, and wherein a selection is operative to determine whether said table should be moved downward vertically or not interlocking with said revolving control means.

9. A radiographic system according to claim 7, wherein:

said lifting control means is operative to move said table downward vertically to the end height at which a downward moving of said table ends.

10. A radiographic system according to claim 7, wherein:

said revolving control means operatively revolves said table until the horizontal level where the table is perpendicular to the vertical direction and then reverse revolving of said table is ended.

11. A radiographic system, comprising;

a radiation source irradiates a radiation;

a table on which a radiographic subject is laid;

a detection means operative to detect the radiation transmitted through the subject, the radiation source and the detection means being in a fixed relative position with respect to each other;

a stand supporting and coupling the radiation source and the detection means to one another;

a revolving means to revolve said table around a revolving axis extending in a width direction of said table;

a revolving direction input means operative to input a direction for revolving of said table;

a revolving control means to operatively control said revolving means according to the input of said revolving direction input means;

a lifting means to move said table revolved by said revolving means in the vertical direction, the lifting means supporting the table and the stand such that when the lifting control means effects movement of the table, the stand, the radiation source, and the detection source correspondingly move;

a lifting control means to control said lifting means to move said table upward vertically when one end of said table comes closer to a floor surface of an external examination room following a revolving of said table in a first direction in accordance with an input of said revolving direction input means;

an input information send control means that sends an input information that is provided to said revolving direction input means and to said lifting control means when an input by which said table revolved in a first direction is revolved in a reverse direction is provided to said revolving direction input means and a revolving angle of the table coinciding with a predetermined end angle is detected;

wherein said lifting control means is operative to move said table downward vertically based on said input information sent from said input information send control means;

wherein said revolving control means operatively revolves said table until the horizontal level where the table is perpendicular to the vertical direction and then a reverse revolving of said table is ended, wherein said revolving direction input means is operative only in the event of that an external operator is operative to continuously conducting an input operation as the direction of revolving is provided; and said revolving control means and said lifting control means are operative to suspend the operation of said table when the input operation is suspended at said revolving direction means.

12. A radiographic system according to claim 11, wherein:

said table revolving control element revolves said table until an end angle that is an angle at which revolving of said table ends, and said lifting control means moves said table downward vertically after revolving of said table reaches to the end angle.

13. A radiographic system according to claim 11, further comprising;

a selection input means, and wherein a selection is operative to determine whether said table should be moved downward vertically or not interlocking with said revolving control means.

14. A radiographic system according to claim 11, wherein:

said lifting control means is operative to move said table downward vertically to the end height at which a downward moving of said table ends.

* * * * *